(12) United States Patent
Jackson

(10) Patent No.: US 7,062,308 B1
(45) Date of Patent: Jun. 13, 2006

(54) REMOTE PHYSIOLOGICAL MONITORING WITH THE RETICULUM OF LIVESTOCK

(76) Inventor: William J. Jackson, 40 Terrace La., Elma, NY (US) 14059

( * ) Notice: Subject to any disclaimer, the term of this patent is extended or adjusted under 35 U.S.C. 154(b) by 400 days.

(21) Appl. No.: 10/190,386

(22) Filed: Jul. 3, 2002

Related U.S. Application Data

(60) Provisional application No. 60/303,204, filed on Jul. 5, 2001.

(51) Int. Cl.
*A61B 5/05* (2006.01)
*A61B 5/00* (2006.01)
*A61B 7/00* (2006.01)

(52) U.S. Cl. .................. 600/361; 600/549; 600/586

(58) Field of Classification Search .............. 600/345, 600/361, 529, 549, 586, 500, 508, 509, 528, 600/300, 301, 372, 373, 377
See application file for complete search history.

(56) References Cited

U.S. PATENT DOCUMENTS

| | | | | |
|---|---|---|---|---|
| 4,262,632 | A * | 4/1981 | Hanton et al. | 119/51.02 |
| 5,158,083 | A * | 10/1992 | Sacristan et al. | 600/361 |
| 5,499,626 | A * | 3/1996 | Willham et al. | 600/300 |
| 5,984,875 | A * | 11/1999 | Brune | 600/549 |
| 6,099,482 | A * | 8/2000 | Brune et al. | 600/549 |
| 6,285,897 | B1 * | 9/2001 | Kilcoyne et al. | 600/350 |
| 6,371,927 | B1 * | 4/2002 | Brune et al. | 600/549 |
| 6,453,199 | B1 * | 9/2002 | Kobozev | 607/40 |
| 6,582,365 | B1 * | 6/2003 | Hines et al. | 600/300 |
| 6,694,161 | B1 * | 2/2004 | Mehrotra | 600/361 |
| 6,754,536 | B1 * | 6/2004 | Swoyer et al. | 607/40 |
| 2002/0042562 | A1 * | 4/2002 | Meron et al. | 600/361 |

FOREIGN PATENT DOCUMENTS

WO   WO 9811816 A1 *   3/1998

* cited by examiner

*Primary Examiner*—Robert L. Nasser
*Assistant Examiner*—Navin Natnithithadha
(74) *Attorney, Agent, or Firm*—Hodgson Russ LLP

(57) ABSTRACT

A system for monitoring physiological parameters within the stomachs of ruminant animals and including two primary interdependent components. Both components are linked by radio frequency communication and software designed specifically for this application. The first component is a sensing transceiver, battery power and electric components hereafter referred to as the device that is tethered by a cord to a weight in the form of a conventional cow magnet. The second component includes both stationary and portable readers/transmitters capable of initiating radio frequency communication with the device(s) for receiving data from them and sending data to them. Software residing in both components utilizes digitized data and operating commands for transmission between the components, for storing selected data and program commands and manipulating the data for viewing, hearing and related analysis.

20 Claims, 1 Drawing Sheet

REMOTE PHYSIOLOGICAL MONITORING WITH THE RETICULUM OF LIVESTOCK

CROSS REFERENCE TO A RELATED APPLICATION

Applicant hereby claims priority based on U.S. Provisional Patent Application No. 60/303,204 filed Jul. 5, 2001 and entitled "Remote Physiological Monitoring Within The Reticulum Of Livestock" which is incorporated by herein by reference.

BACKGROUND OF THE INVENTION

This invention relates to the art of indwelling sensors for ruminant animals, and more particularly to a new and improved device and method for monitoring selected physiological parameters from within the stomach of ruminant livestock using radio frequency telemetry and external readers and transmitters.

One area of use of the present invention is detecting metabolic diseases in ruminant livestock, although the principles of the invention can be variously applied. Metabolic diseases in ruminant livestock can develop in several forms with different clinical signs and methods of treatment. One of the most common forms is rumen acidosis which may occur in sheep and goats but which has the greatest economic impact when occurring in adult dairy and beef cattle. Symptoms result from the sudden and excessive intake of rapidly fermentable carbohydrates producing a sudden drop in rumen pH below 5.0, and death can occur as rapidly as within 2–5 days.

A second form, subacute rumen acidosis, also known as SARA, has similar origins to the acute form but presents different symptoms and disease progress. SARA is prevalent in both the beef feed lot and the large confinement dairy operations, and it has the greatest economic consequences of all the metabolic disorders. The presence of SARA can be confirmed by invasive methods removing a sample of rumen fluid and immediately testing the pH level. Normal pH levels range from 5.8 to 6t. Serious harmful effects may result over time if affected cows cannot naturally compensate or receive treatment for a pH that declines to and sustains at 5.8 and lower levels such as 5.4. Cattle with SARA complications typically have depressed feed intake and fail to gain weight at the normal rate. SARA affected milking cows show a decline in milk production and have depressed butter fat levels.

When a general examination of a herd suggests the presence of SARA, due to externally visible symptoms, it has been possible to make quantifiable measurement of the rumen pH using one of three methods. In the event the pH is found to be below the desired level, feed formulation changes may be introduced using various buffering agents and other supplements to normalize the rumen pH.

One method, typically employed at research farms, is surgically fitting the cow with a fistula or cannula which is a permanently fixed porthole surgically established in the left topside of the cow giving direct access to the rumen. The opening is equipped with a soft removable plug which allows entry of suction devices to extract rumen samples for pH measurement or placement of an in dwelling pH electrode suspended into the rumen fluid. This procedure is obviously expensive, and while fairly common at research farms is not practical for commercial dairy farms.

Another method utilizes an orally administered flexible tube passed down the esophagus into the reticulum or through the rumen whereby rumen fluid is drawn into the tube which then is removed from the animal for an immediate pH level test. While this method is relatively simple and quick it suffers from the limitations of need to restrain the animal, lack of assurance that the fluid always is drawn from the same location in the rumen each time or from the most important area of the lumen, and the chance that the sample is compromised by saliva containing buffering agents involuntarily released by the animal during the procedure.

The third procedure, heretofore thought to be the most accurate, is known as rumenocentesis wherein a syringe is inserted through the abdominal lower left sidewall of the animal into the rumen cavity for immediate withdrawal of rumen fluid to be pH tested. This has been the recommended method for use on commercial farms and is highly reliable if done properly. However, it is time consuming and expensive due to the need for several people to restrain the animal and the need to surgically prepare the penetration site. Also, there is some risk of infection at the site.

While the foregoing describes metabolic illnesses found in domestic livestock, there are other livestock health problems which call for a device and method for diagnosing and monitoring the animal during a course of treatment.

SUMMARY OF THE INVENTION

There are two primary interdependent components associated with this invention. Both components are linked by radio frequency communication and software designed specifically for this application. The first component is a sensing transceiver, battery power and electric components hereafter referred to as the device that is tethered by a cord to a weight in the form of a conventional cow magnet. The second component includes both stationary and portable readers/transmitters capable of initiating radio frequency communication with the device(s) for receiving data from them and sending data to them. Software residing in both components utilizes digitized data and operating commands for transmission between the components, for storing selected data and program commands and manipulating the data for viewing, hearing and related analysis.

The following detailed description of the invention, when read in conjunction with the accompanying drawing, is in such full, clear, concise and exact terms as to enable any person skilled in the art to which it pertains, or with which it is most nearly connected, to make and use the invention. The advantages and characterizing features of the present invention will become clearly apparent upon a reading of the following detailed description together with the accompanying drawing.

DETAILED DESCRIPTION OF THE INVENTION

Figure 1:
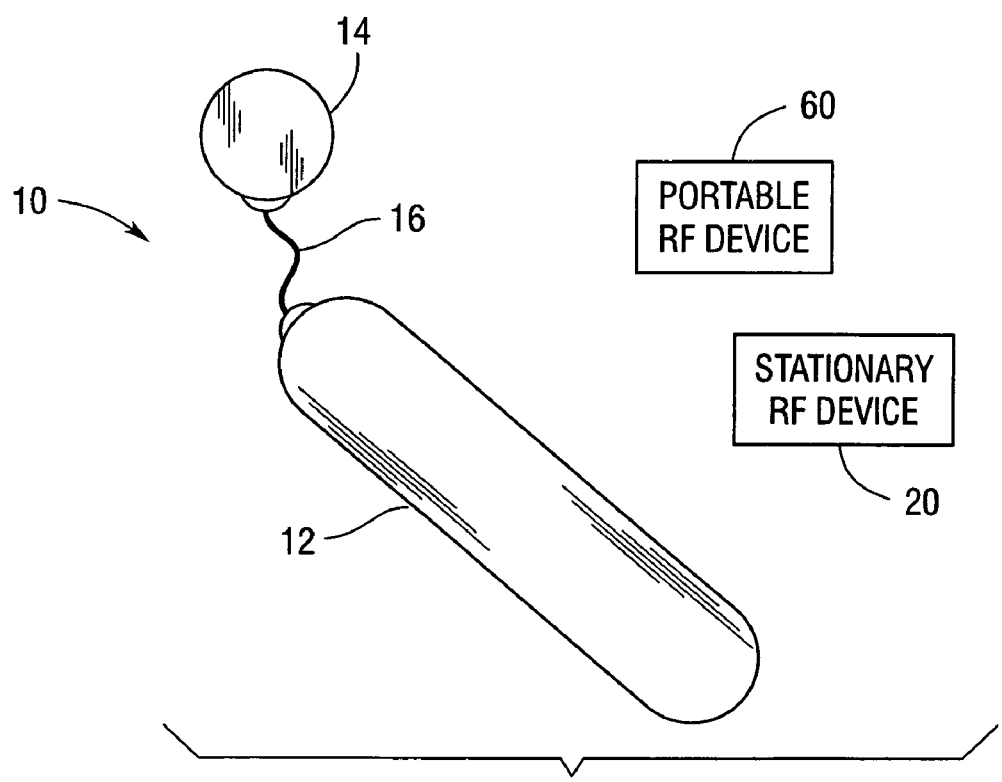
FIG. 1 is a diagrammatic view of the system and device according to the present invention.

Referring to FIG. 1, the system of the present invention comprises a device 10 which includes a weight in the form of a conventional cow magnet 12, a sensor unit 14 and an umbilical connector in the form of a cord 16 connecting magnet 12 and sensor 14 together. The device 10 is implanted with a conventional "balling gun" into the upper throat of the host where after it is swallowed passing into the reticulum chamber of the stomach. There it will reside safely for the life of the host sensing, receiving, storing and transmitting data on demand by external complementary reader/transmitter equipment 20. The tether 16 will allow the sensor portion 14 of the device to lift and float away from the heavier magnet 12 that will settle to the lower reaches of the reticulum. The floating sensor portion 14 will have greater exposure to the reticulum contents enabling it to perform its intended functions with the ingesta. The device 10 will be fully recoverable during the rendering process at the time of slaughter owing to the connection to the cow magnet. This feature is anticipated to comply with USFDA Feed Additive regulations pertaining to the use of implants in livestock.

The sensor unit 14 contains various electronic components and a transceiver that enables it to monitor selected physiological processes, store data from the sensors and from external sources and communicate with external reader/transmitters 20 using radio frequency (RF) communication technology. Space can be provided on the printed circuit board in sensor unit 14 for additional sensors at a future date. Each sensor unit 14 contains a microchip programmed with the manufacturer's installed software to store, process and control the unique identification code, the sensing activity, the timer and the pH calibration functions. The microchip has a read/write capability. External reader/transmitters 20 have a write capability and a write program to transmit external data and commands to the microchip of sensor unit 14 as read only data for future referral purposes.

Read only data can include host genetic history, date of birth, breed registration, ownership, date of sale, breeding activity, critical health illness and injury events, sensitive medications administered, and production records. Data input capability is established in software programs provided within external reader and transmitter computers 20. Each device sensor unit 14 will have an unalterable unique identification code established on the microchip at the time of manufacture that can be read only on demand by associated external readers. The sensor unit 14 has a temperature sensor to identify the surrounding ingesta temperature. Temperature data can be periodically measured and stored on the device microchip. On demand, this stored data can be transmitted to the external readers 20. Also on demand, temperature can be sensed in real time and transmitted directly from the sensor unit 14 to external readers 20.

The sensor 14 has a pH "ISFET" sensor coupled with a pH calibration element to compensate for pH drift. The pH sensing of the surrounding ingest can be periodically measured and adjusted for the prevailing temperature and stored on the sensor unit microchip. On demand this stored data can be transmitted to the external readers 20. Also on demand, pH data can be sensed in real time and transmitted directly from the sensor unit 14 to external readers 20.

Figure 2:
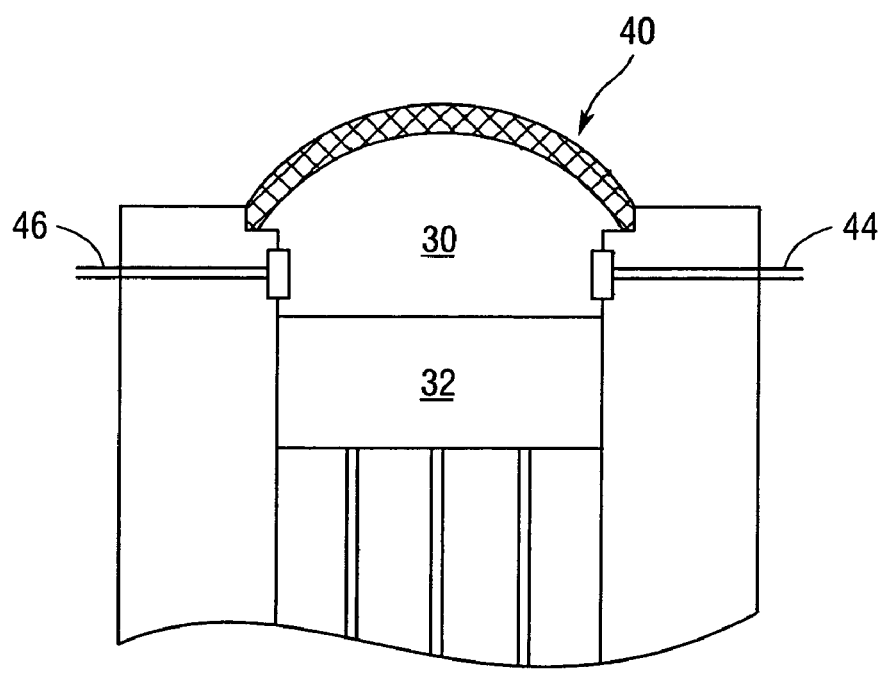
FIG. 2 is a fragmentary diagrammatic view of the sensor in the device of FIG. 1.

A form of pH sensor and associated calibration elements is shown in FIG. 2. The pH calibration uses a small chamber 30 between the pH sensor 32 and the outside ingesta contents of the stomach. A diffusion barrier between the chamber and the outside allows only a slow access (or exchange) of H+ ions into the chamber to be sensed. A domed cap 40 forms the exterior of the diffusion chamber 30. It consists of a stainless steel screen coated with a silicon rubber antifouling material. With the chamber is a set of electrolysis electrodes (silver anode 44 and a gold cathodeproportion 46). When a current is passed between the electrodes, OH− is produced that will react with the H+ in the chamber 30 in a classic acid/base titration/neutralization reaction. The reaction progress is monitored by the pH sensor 32 and the net change (current-time product) is recorded. When the pH is increased to pH=7 (or another end point) the neutralization of the H+ which was in the chamber 30 is considered complete and the net change is noted. Since the chamber volume is known, the true initial pH (before the current was turned on) can be calculated. The difference between the true pH and the apparent pH (pH measured by the sensor) is the zero offset. The sensor electronics is then corrected for the zero offset and used for subsequent pH measurements. It will take some time for the sensor 32 and the chamber 30 to recover from the electrolysis calibration process due to the slow diffusion of the H ion across the barrier 40 While pH data will be collected periodically throughout a 24 hour period, calibration will be required on a weekly basis to compensate for the drift factor.

The sensor unit 14 optionally can contain a sound sensor microphone to pickup the host's heartbeat, respiration, and rumen contraction vibrations. These sounds can be sensed in real time and on demand transmitted directly from the sensor unit 14 to external readers 20. The sensor unit 14 also can contain a sequential timing device that will be activated at the time of placement in the host. A time cycle will include the (year, month, day, hour and minute) will be input to the microchip by the external reader 20 when device is initially activated in the host. Thereafter, the accumulation of time in minutes in relation to the sensed and stored data as well as permanently recorded data will be available to external readers 20 on demand.

The sensor unit 14 has a battery to energize the timer, the sequence of programmed sensing of temperature and pH and the recording of data on the microchip. Sensing activity can be shut down to a sleep mode on demand from external transmitters 20 to conserve battery power. The sensor unit 14 has an RF transponder to send and receive data with external receiver/transmitters 20.

The stationary external reader/transmitters 20 are radio frequency equipment coupled with data loggers and placed in permanent facility locations where the host animals reside. Coupled to this equipment is a computer with resident software for communicating with the individual active devices in the host animals. Allied with the computer are a monitor, sound speakers and a keyboard for the user to make observations and send data and commands to the devices 10 in the host animals. Alternatively a direct connection to the internet will allow these functions to be performed at a remote location.

The stationary external reader/transmitters 20 will activate internal sensor data stored on the device microchip or retrieve data that is accessible in real time by way of radio frequency energy when the host comes into close proximity to the stationary equipment 20. Resident software in these stationary systems manipulates the incoming data displaying it and if desired storing the host identification code, temperature and pH information residing in the microchip. These reader/transmitters 20 with the associated data logger and computer equipment are programmed to digitize sensor derived data and display it as stand alone numerical values, in a table format or in graphic display. Data described above can be recalled and read only by this equipment. The stationary readers can equipped with audio speakers to amplify the real time sounds detected and transmitted by the microphone in sensor unit 14 for monitoring internal sounds such as heart beat, respiration and rumen contractions.

The stationary readers 20 can be connected to keyboards to enable data input to the sensor unit microchip for such functions as initiating sensing functions, recording unique information described above for later read only purposes. Data gathered from the sensor units of the indwelling devices 10 may be stored in this external computer resident memory or transferred to other computer files for future integration with programs for management and/or research purposes.

The system of this invention can include portable, handheld readers/transmitters, one designated 60 in FIG. 1, to permit recognition of a particular animal. Portable reader/transmitter equipment 60 is in the category of laptop and hand held computers with the added radio frequency and data logger capability to communicate with the devices 10 in the host animals. They are self-contained battery powered and carried about where the animals reside. The portable equipment 60 is designed and programmed to receive stored and real time data in the same manner as the stationary variety. Equipped with speakers and or earphones they are capable of receiving the sound detected by the sensor unit microphone. If they contain a keyboard they will be able to transmit data for storage on the read only sensor unit microchip. If they are adequately powered they can perform all of the functions as the stationary counterparts described above.

Appropriate software is provided to operate the functions within the internal components, i.e. sensor units 14, and the external components i.e. readers 20 and 60. Data stored in either environment will have a file format that permits it to be merged with other related data files.

The invention is illustrated further by the following description of a typical application in the dairy industry. The sensing component 14 with the attached cow magnet 12 will be introduced to the female dairy cow about one month before the first calving event. Breeding bulls that will be turned loose among the female cows may also have the device implanted at about the same chronological age as their female herd-mates. At the time the device 10 is implanted the sensor 14 will be turned on by the companion external stationary 20 or portable equipment 60 and tested for the basic operations of sensing temperature and pH by placing the sensor body in a known pH solution. When acceptable readings are verified including the unique sensor identification code, the sensor 14 with the attached tethered magnet 12 will be placed in a jel-cap, and loaded into a balling gun for insertion in the host animal.

The host will be restrained in a headlock, the loaded balling gun inserted to the back of the mouth where the throat begins and the jel-cap discharged into the upper esophagus. Confirmation is made that the contents of the jel-cap are fully swallowed to the reticulum by externally locating the magnet 12 with an external magnetic sensitive instrument held in the region next to the reticulum. A hand held directional compass often provides this assurance. In the event the jel-cap has not been fully ingested a quantity of drenching fluid can be administered to the animal to facilitate the swallowing process.

The jell-cap will dissolve in a couple of minutes. Thereafter, the external reader 20 or 60 should communicate with the ingested sensor 14 to verify the recorded identification code, temperature, pH and monitor the microphone sounds. When these functions respond affirmatively the other animal history data can be communicated to the microchip of sensor 14 from the external keyboard of the reader 20 or 60 The predetermined regular sensing of temperature and pH can be activated in this early period to establish the acidity of the rumen contents and if in the normal range form a base line for future reference.

These first time host female ruminant animals are typically housed in separate quarters from the lactating heard mates and breeding bulls. In this period they are fed a lower carbohydrate ration. Data collected from stationary readers 20 in this area will monitor their rumen pH and temperature. One of the looked for signs for the onset of calving is a one degree drop in body temperature. If this is detected on the external monitor 20 the host mother should be quartered in a maternity space. In this location, stationary monitors 20 and associated loud speakers maybe employed to monitor heart rate and respiration in real time as well as temperature.

Following the calving event, the host is moved to another quarter where the high group of lactating cows are housed and fed a more carbohydrate rich ration to maximize milk production. In this setting, the risk of metabolic acidosis is most likely to occur in the first four months following the calving event. Routine monitoring of the pH of the rumen contents will provide an early indication of a manageable acidosis problem if steps are taken to alter the animal ration and or add buffering supplements for them to consume. In this period, the sensor 14 will be programmed to monitor the pH and temperature several times an hour and store the data on the sensor's microchip. The implanted sensor 14 will be polled by an external reader each time the host cycles through the milking parlor, (2 or 3 times in 24 hours). The internal stored data will be downloaded to the external computer 20. Observations by a trained person will permit them to identify the onset of distress from an acidosis problem as well as other undesirable consequences from an infection or another health disorder.

A goal for dairy operators is to rebreed a lactating animal about sixty days after a calving event. A one-degree rise in temperature along with other outward symptoms is a good indicator of the presence of the estrus cycle. Monitoring the temperature regularly each hour throughout this four-month period will be a helpful indicator of this often undetected, short-term, economically critical event.

At a predetermined time, the herd manager may selectively shutdown the internal monitoring functions for pH and temperature to conserve battery power. This may be done when it is determined that the health risks to the animal have subsided and she has been successfully rebred. It is thought that this can occur about four months after calving if there are no adverse health problems. This monitoring process can be reactivated in the month preceding the next calving event.

Female cows and breeding bulls are exposed to a variety of injuries and illnesses. Having an indwelling device that can monitor the vital signs of temperature, heart rate, respiration and rumen contractions without having to catch and restrain the subject to perform a hands on examination will be a time saving and a safety benefit for the animal as well as the people who supervise their care. Implanted animal monitoring activity can be performed by the external stationary 20 or portable equipment 60 programmed to poll the implanted device 10 to read and hear in real time the selected vital signs. If these remote hands-off results indicate an underlying problem it maybe necessary to catch and restrain the subject for closer examination and treatment.

Space is sufficient in the sensor microchip to permit the permanent recording of non-erasable unique information that the owner determines to have reside with the animal until it is sold or disposed of. This additional data that may be of some future value includes production results, sire bred to, date pregnancy was confirmed, date she calved, illness or injury events, medication protocol administered, and sale date. At any point this information can be viewed on the external component equipment 20, 60 and downloaded for a permanent record.

While an embodiment of the present invention has been described in detail, that is for the purpose of illustration, not limitation.

The invention claimed is:

1. A device for monitoring at least one physiological parameter from within the stomach of ruminant animals comprising:
   a) a sensor component for obtaining physiological data and providing the data in a form accessible from an external location by radio frequency communication;
   b) a weight component of a size and shape for introduction to the stomach of a ruminant animal, the weight component comprising a cow magnet; and
   c) a cord connecting the sensor component and the weight component to each other;
   d) so that as the weight component settles to a location in the stomach the cord tethers the sensor component to float in spaced relation to the weight component.

2. The device according to claim 1, wherein the sensor component comprises a pH sensor.

3. The device according to claim 1, wherein the sensor component comprises a temperature sensor.

4. The device according to claim 1, wherein the sensor component comprises an acoustic sensor to monitor heartbeat, respiration and rumen contraction vibrations.

5. The device according to claim 2, wherein the pH sensor comprises:
   a) a sensor housing:
   b) a chamber defined in the housing;
   c) a pH sensing device in communication with the chamber; and;
   d) a diffusion barrier to allow slow flow of ions between the chamber and a medium being monitored for pH.

6. The device according to claim 5, further including anode and cathode electrodes in communication with the chamber for establishing a reaction in the chamber for measurement of pH.

7. A system for monitoring at least one physiological parameter within the stomach of at least one ruminant animal comprising:
   a) a device for introduction into the stomach of the animal and comprising a sensor for obtaining physiological data and providing the data in a form accessible by radio frequency communication, a weight component of a size and shape for introduction to the stomach of the animal and for settling by gravity to a low region of the stomach, the weight component comprising a cow magnet, and a cord tethering the sensor to the weight component; and
   b) a radio frequency communication device located external to the animal for communicating with the device to obtain the physiological data.

8. The system according to claim 7, wherein the radio frequency communication device comprises a transceiver.

9. The system according to claim 7, wherein the device includes a transceiver operatively associated with the sensor.

10. The system according to claim 7, wherein the radio frequency communications device is fixed at a location so as to be stationary.

11. The system according to claim 7, wherein the radio frequency communications device is portable.

12. The system according to claim 7, including a plurality of devices for introduction into the stomachs of a corresponding plurality of animals and wherein the sensor of each device is provided with a unique identification code for access by the radio frequency communications device.

13. The system according to claim 7, wherein the sensor has data storage capability.

14. The system according to claim 7, wherein the radio frequency communications device has data storage capability associated therewith.

15. A method for monitoring at least one physiological parameter within the stomach of at least one ruminant animal comprising:
   a) introducing into the stomach of the animal a device comprising a sensor for obtaining physiological data and providing the data in a form accessible by radio frequency communication and a weight of a size and shape for introduction to the stomach of the animal and for settling by gravity to a low region of the stomach, the weight comprising a cow magnet, and a cord tethering the weight to the sensor; and
   b) accessing data from the sensor externally of the animal utilizing a radio frequency communication device.

16. The method according to claim 15, wherein the device is introduced to the stomach of the animal by:
   a) restraining the animal;
   b) placing the device in a jell capsule; and
   c) discharging the encapsulated device into the upper esophagus of the animal using a balling gun inserted in the back of the animal's mouth.

17. The method according to claim 15, further including providing a plurality of devices for introduction to the stomachs of a corresponding plurality of animals and providing each sensor with a unique identification code for access by the communication device.

18. The method according to claim 15, further including providing the sensor with data storage capability and downloading data from the sensor during accessing by the communication device.

19. The method according to claim 17, further including providing a portable radio frequency communication device and locating a particular animal by moving the communication device to different locations.

20. A method for monitoring at least one physiological parameter within the stomach of at least one ruminant animal comprising:
   a) introducing into the stomach of the animal a device comprising a sensor for obtaining physiological data and providing the data in a form accessible by radio frequency communication and a weight of a size and shape for introduction to the stomach of the animal and for settling by gravity to a low region of the stomach and a cord tethering the weight to the sensor;
   b) the device being introduced to the stomach of the animal by restraining the animal, placing the device in a jell capsule, and discharging the encapsulated device into the upper esophagus of the animal using a balling gun inserted in the back of the animal's mouth; and
   c) accessing data from the sensor externally of the animal utilizing a radio frequency communication device.

* * * * *

UNITED STATES PATENT AND TRADEMARK OFFICE
CERTIFICATE OF CORRECTION

PATENT NO.        : 7,062,308 B2                                         Page 1 of 1
APPLICATION NO. : 10/190386
DATED             : June 13, 2006
INVENTOR(S)       : William J. Jackson It is certified that error appears in the above-identified patent and that said Letters Patent is hereby corrected as shown below:

On the title page,

[*] Notice:    Subject to any disclaimer, the term of this patent is extended or adjusted under 35 USC 154(b) by (400) days Delete the phrase "by 400 days" and insert - by 395 days—

Signed and Sealed this

Fifth Day of September, 2006

JON W. DUDAS
*Director of the United States Patent and Trademark Office*